US00PP12771P2

(12) United States Plant Patent
Jacob

(10) Patent No.: US PP12,771 P2
(45) Date of Patent: Jul. 16, 2002

(54) NON-DWARFING PEAR ROOTSTOCK NAMED 'RHENUS 3'

(76) Inventor: Helmet B. Jacob, Nachtigallenweg 15, Geisenheim (DE)

( * ) Notice: Subject to any disclaimer, the term of this patent is extended or adjusted under 35 U.S.C. 154(b) by 0 days.

(21) Appl. No.: 09/240,184

(22) Filed: Jan. 29, 1999

(51) Int. Cl.[7] ..... A01H 5/00
(52) U.S. Cl. ..... Plt./179
(58) Field of Search ..... Plt./179

*Primary Examiner*—Bruce R. Campell
*Assistant Examiner*—Michelle Kizilkaya
(74) *Attorney, Agent, or Firm*—Klarquist SparkmanLLP

(57) ABSTRACT

A new and distinct variety of *Pyrus communis* named 'Rhenus 3' that is compatible as a rootstock with all pear varieties tested and when used as a rootstock for pear varieties, does not cause significant dwarfing. When used as a rootstock, 'Rhenus 3' results in high yield efficiency, early yield (precocity), substantially uniform fruit size, high frost hardiness, no suckering, and good soil adaptation.

4 Drawing Sheets

BACKGROUND OF THE INVENTION

The present invention comprises a new non-dwarfing rootstock for pears (*Pyrus communis*) designated 'BU/233' for experimental purposes and now referred to by the varietal name 'Rhenus 3'.

The new variety was selected by me in a cultivated area in a orchard at the Research Station of Viticulture and Horticulture in Geisenheim, Germany. Pear varieties 'Old Home' (female) (unpatented, believed to be publicly available) and 'Bonne Louise d'Avranches' (male) (unpatented, believed to be publicly available) were cross-pollinated and a substantial number of the resulting seeds were germinated. A number of seedlings were then used as rootstocks for pear varieties grafted onto the rootstocks. The grafted seedlings including 'Rhenus 3' were then evaluated as rootstocks. 'Rhenus 3' was then selected for further testing.

'Rhenus 3' has not been observed under all possible environmental conditions and its phenotype may vary significantly with variations in environment such as temperature, light intensity, and day length, without any variation in genotype. However, the following unique combination of characteristics relating to the use of 'Rhenus 3' as a rootstock for pear varieties, distinguish 'Rhenus 3' from all other pear varieties of which I am aware: (1) causes non-dwarfing of pear varieties; (2) compatible as a rootstock with all pear varieties tested; (3) high yield efficiency; (4) early yield (precocity); (5) substantially uniform fruit size; (6) high frost hardiness; (7) no suckering; (8) good soil adaptation; and (9) easy propagation from hardwood and softwood cuttings. These characteristics are established and transmitted through succeeding asexual propagations.

Asexual reproduction of 'Rhenus 3' is accomplished, for example, by tissue culture; softwood and hardwood cuttings, e.g., using 2,000 ppm indole-3-butyric acid (IBA) (quick dipping) by the "methode Trefoise" (R. Trefoise, "Description des techniques de bouturage feuille des nouveaux sujets porte-greffe nanifiants dur cerisier," *Note technique du Centre de Recherches Agronomiquies de l'Etat Gembloux*, No. 10/50, Septembre 1988, I.S.S.N. 0771–0607, 1988).

BRIEF DESCRIPTION OF THE DRAWINGS

The following drawings are photographs of 'Rhenus 3' taken at the Research Station of Viticulture and Horticulture in Geisenheim, Germany, except for FIG. 3 which was taken in Dundee, Oreg.

DETAILED DESCRIPTION OF THE PREFERRED EMBODIMENTS

The following is a detailed description of the invention based on plants grown at the Research Station of Viticulture and Horticulture in Geisenheim, Hessen, Germany (hereinafter, "the Research Station") and in Dundee, Oreg. Color descriptions and other terminology are used herein in accordance with ordinary dictionary significance unless otherwise noted with reference to The Royal Horticultural Society Colour Chart (R.H.S.). It should be noted that color does vary with time of year, lighting conditions, and soil and nutrient conditions. For example, leaf colors tend to be brighter green if the plants are grown in soil with greater nitrogen concentrations, and to be more yellow when grown in soil containing lesser amounts of nitrogen.

All trees of the 'Rhenus 3' variety, insofar as I have been able to observe them, have been identical in all the characteristics described below.

Propagation: Holds to distinguishing characteristics through succeeding propagation by rooted cuttings.

Figure 1:
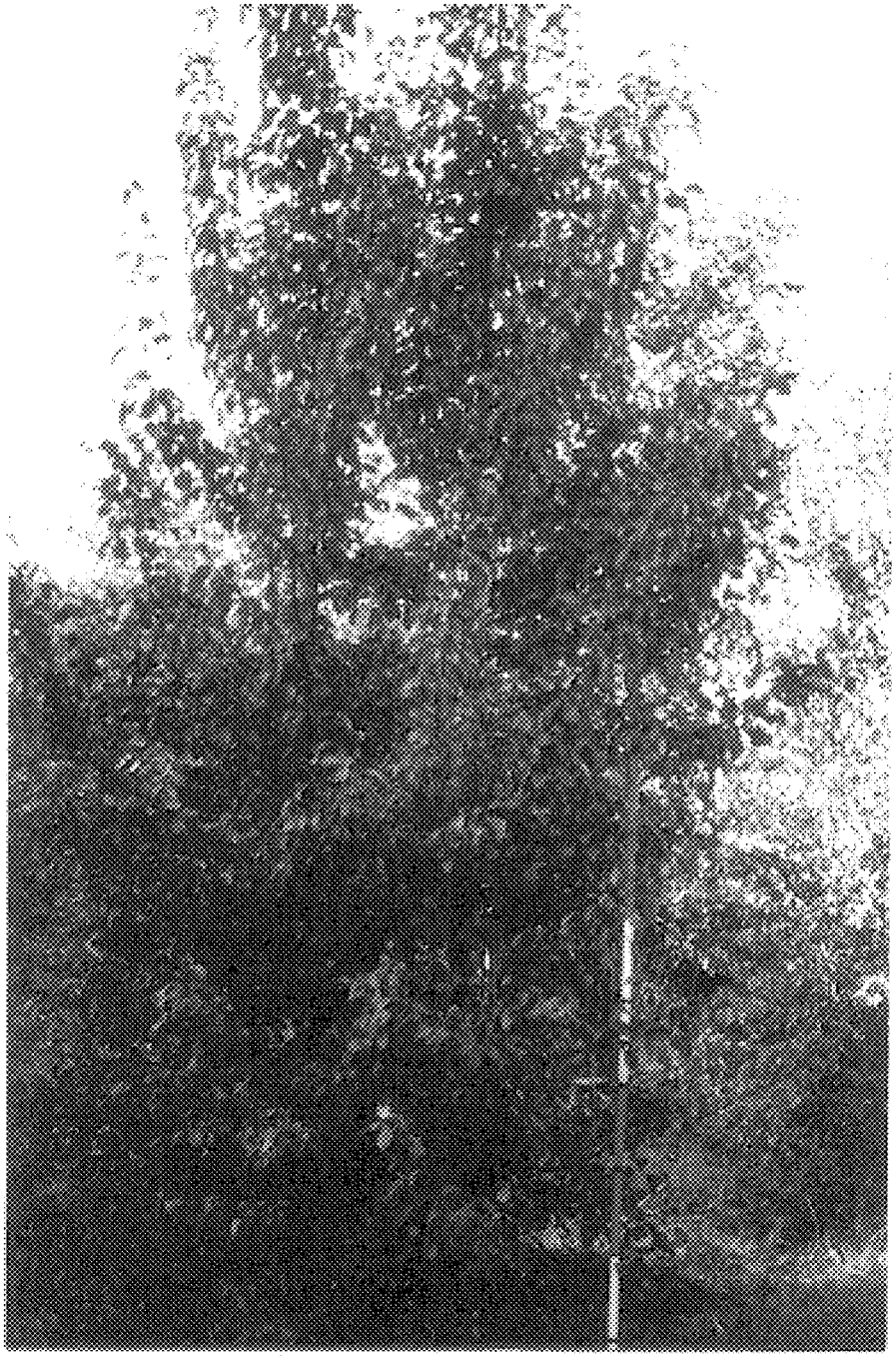
FIG. 1 is a view of five-year-old nonpruned specimen of 'Rhenus 3' (height: about 5 m).
Figure 2:
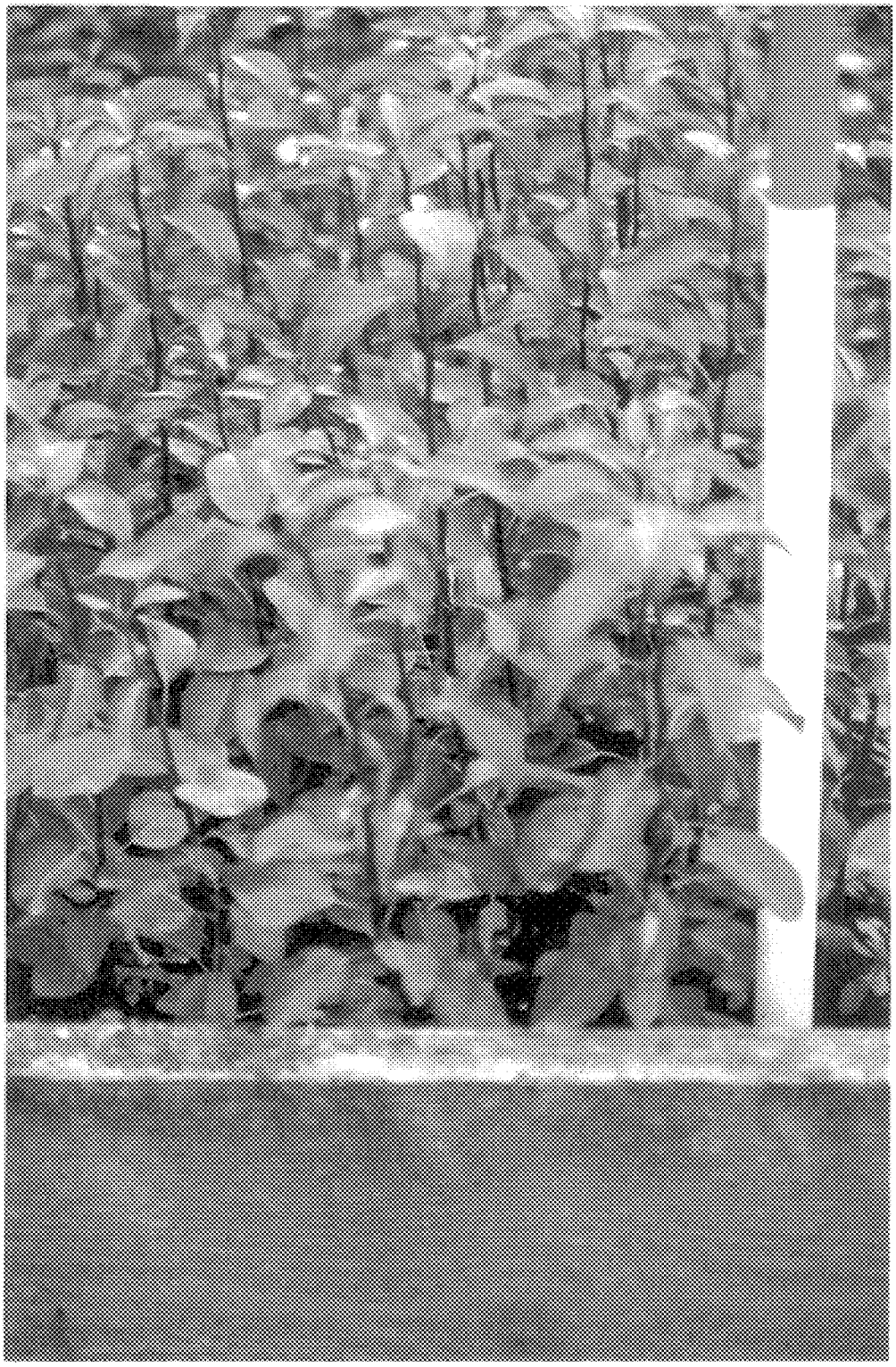
FIG. 2 shows rooted hardwood cuttings of 'Rhenus 3'.

Tree (non-grafted):

*Trunk.*—Size: Full size. Height: After five years, non-grafted 'Rhenus 3' trees range from 4.5 m to 5.5 m (FIG. 1 shows a five-year old nonpruned specimen with a height of about 5 m.); by comparison, vigorous pear trees, e.g., 'Bartlett', are commonly 5 to 7 m when grown under the same conditions and U.S. Plant Pat. Ser. No. 11,041) 'Rhenus 1' trees range from 2.0 to 2.5 m. Circumference: After five years, in our test BU 2/33 trees had a circumference of 160 mm in comparison to 'Rhenus 1' trees of the same age having a circumference of about 80 mm. Bark Surface Color: Greyed-brown (two-year-old trunk bark color like RHS 199A). Surface Texture: Smooth. Form: Spread upright.

*Branches.*—Size: Little, slight. Surface Texture: Smooth. Bark Color: Greyed-brown. New Growth Color: Bright green. Mature One Year Growth Color: Greyed-brown (like RHS 197A for bark of mature one year branches taken in the fall from a 'Rhenus 3' plant growing in Dundee, Oreg.). By mature one year branches, it is meant branches that have grown throughout the summer of a single growing season. Internode Length: 18–25 mm. Lenticels: Yellow-white, larger than 'Rhenus 1', elongated in direction of longitudinal axis of branch on mature one-year-old branches.

Figure 3:
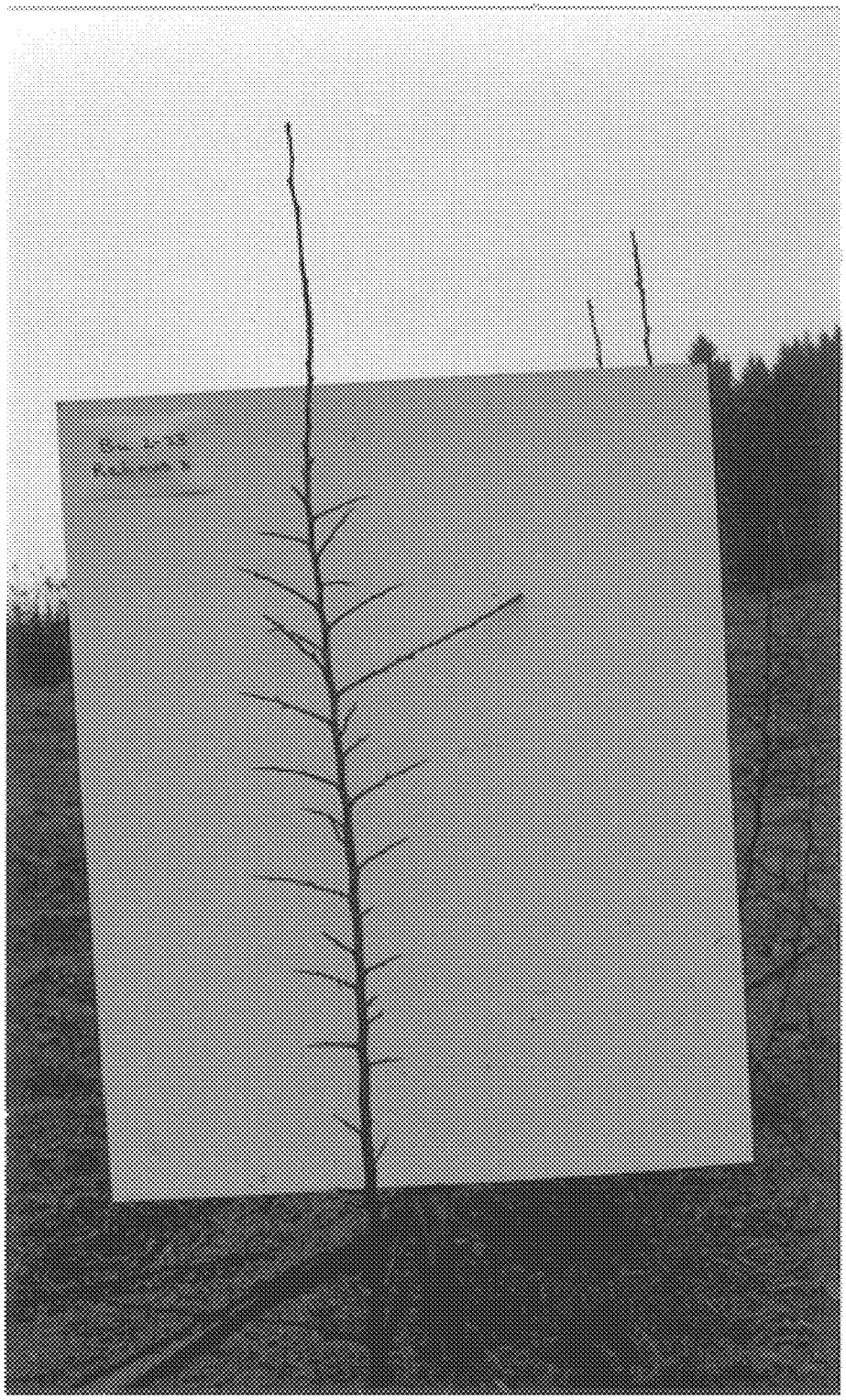
FIG. 3 shows a dormant 'Rhenus 3' tree that was planted in July 1997 as a tissue culture plant.
Figure 4:
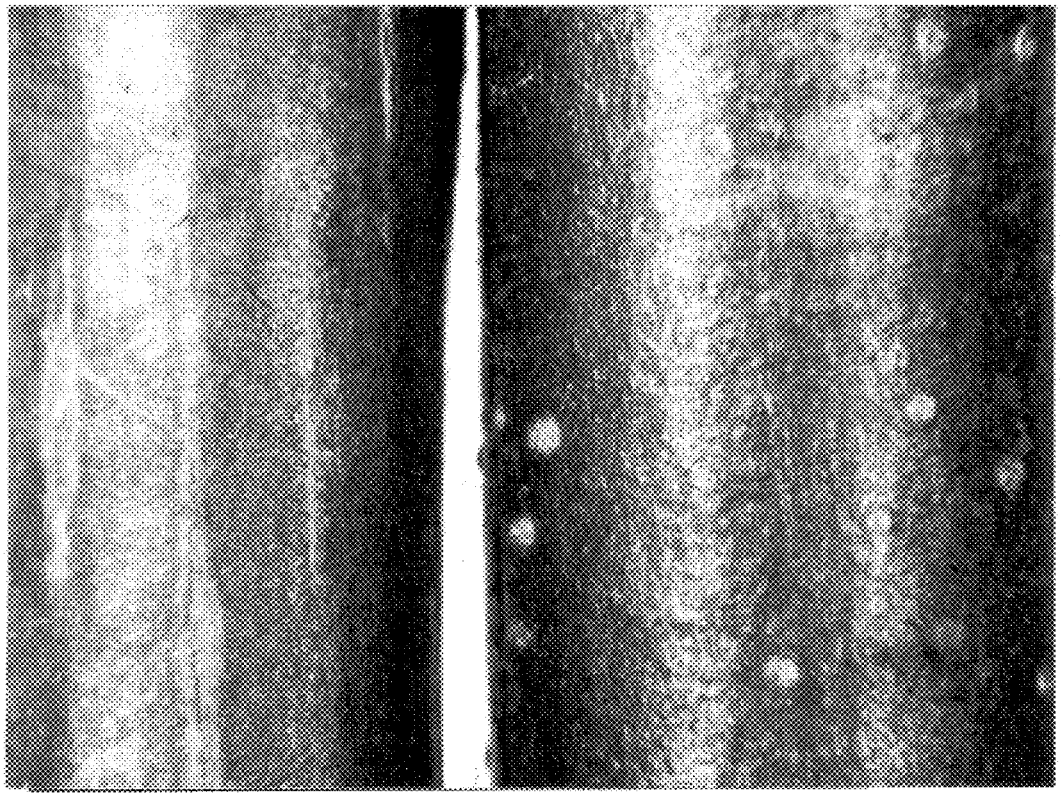
FIG. 4 shows a comparison of the bark and lenticels of one year old 'Rhenus 3' branches (on the left in this figure) with one year old 'Rhenus 1' branches (on the right in this figure).

*Leaves* (See FIG.3).—Size: Small. Length averages 50–60 mm, including the petiole. Width averages 28–32 mm. Surface Texture: Normal for the species. Form: Linear-elongated. Color: Upper surface is bright to dark green. Lower surface is bright grey-green. Mid-vein: Size: average. Color: yellow-green. Petiole: Length: Normal for species, 8–10 mm. Thickness: 0.3–0.5 mm. Color: Yellow-green to brown (like RHS 147A for fall leaves from a 'Rhenus 1' plant growing in Dundee, Oreg.). Leaf glands: none.

*Flowers.*—The original non-grafted 'RHENUS 3' plant had flowers four years after planting. The following observations of the bloom of 'RHENUS 3' was made in Dundee, Oreg., on Apr. 19, 2001. Petals: Five petals per bloom, approximately 11 mm. long and 7 mm. wide, approximately 2 mm. at the apex and 1 mm at the base. Petal Color: Pure white (RHS 155D). Peduncle: Length about 7 mm. Sepal: Length about 6 mm; with at apex is about 0.5 mm and about 2 mm at the base. The center of the sepal is about 1.5 mm wide. Sepal color: Yellow-green (like RHS 155A). Anthers: 20 per bloom. Start as red-purple color (RHS 66B) and soon turn black (RHS 200A). Stigmas: 5 stigmas per bloom. Fragrance: The bloom has a musty odor. Fruit: Non observed.

*Performance as rootstock when grafted.*—Growth Characteristics: Non-dwarfing when used as a rootstock. Greater than quince C and quince A; trunk size of grafted Bartlett (unpatented) pear trees twice as large as when 'Rhenus 1' used as a rootstock (see Table 1). Root Sprouts (suckering): None in seven years. Anchorage: Very good. Compatibility: Very good. No incompatibility observed with any pear variety. Fruit size: When used as a rootstock for 'Bartlett' pear, greater than ninety percent of the fruit being in excess of 60 mm diameter in one observation.

*Soil adaptation and tolerance.*—Chlorosis: No problems observed. Wet: No problems observed.

*Pathogen resistance.*—Moderately tolerant to fire blight. Very tolerant to powdery mildew.

'Rhenus 3' rootstock has been found not to significantly reduce scion shoot growth (e.g., as measured by trunk circumference) of 'Bartlett', a commercially important pear variety. As shown in Table 1 for 'Bartlett' scions grafted to 'Rhenus 3' and various other rootstocks, 'Rhenus 1' rootstock is about fifty percent more dwarfing than 'Rhenus 3' rootstock. OHxF rootstock (not patented, publicly available), quince A rootstock, and quince C rootstock are also far more dwarfing than 'Rhenus 3'.

Moreover, 'Rhenus 3' does not appear to significantly reduce fruit size. Fruit from 'Bartlett' trees grafted to 'Rhenus 3' rootstock is larger than fruit from 'Bartlett' grafted to quince A and grown under similar conditions and is comparable to fruit grown on 'Rhenus 1' rootstock (see Table 2).

In addition, 'Rhenus 3' rootstock confers precocity on grafted pear varieties, even though it has previously proven difficult to force precocity on pears. Pear varieties that are grafted to 'Rhenus 3' rootstock have a shorter juvenile stage, apparently shutting down vegetative growth early, and form fruit buds on the shoot tips. For example, 'Bartlett' pear trees grafted to 'Rhenus 3' rootstock can bear fruit in as little as three to four years, compared with seven years for self-rooted 'Bartlett' pear trees.

'Rhenus 3' also displays high frost hardiness, i.e., is able to withstand cold winter temperatures (−15° C. for fifteen days) without substantial freezing damage.

COMPARISON TABLES

Table 1 provides data regarding the growth (trunk circumference) and yield efficiency (or productivity) of 'Bartlett' grafted to 'Rhenus 3' and other rootstocks. Trunk circumference measurements are made 10–20 cm above the graft union on grafted trees. Table 2 provides data regarding fruit size grades and total fruit weight and number of 'Bartlett' grafted to 'Rhenus 3' and other rootstocks.

TABLE 1

Growth and Yield Efficiency of Bartlett Pears Grafted on Various Pear Rootstocks

| ROOT STOCK | Yield (kg) 1986 | 1987 | 1988 | 1989 | 1986-1989 | TOTAL TRUNK CIRCUM-FERENCE *(mm) | YIELD EFFI-CIENCY ** |
|---|---|---|---|---|---|---|---|
| EM QUINCE A | 0.0 | 1.7 | 11.1 | 14.2 | 27.0 | 105 | 25.7 |
| EM QUINCE C | 1.3 | 7.1 | 9.1 | 8.2 | 25.8 | 73 | 35.2 |
| OHxF 333 | 0.0 | 3.1 | 7.3 | 7.0 | 17.4 | 119 | 14.6 |
| Rhenus 3 | 11.3 | 14.4 | 17.1 | 19.2 | 62.0 | 160 | 38.7 |
| Rhenus 1*** | 0.9 | 2.5 | 17.6 | 19.8 | 40.8 | 80 | 51.0 |

*Six years after planting

**

$$\text{Yield efficiency (kg/mm)} = \frac{\text{Total Yield 1986-1989}}{\text{Trunk circumference}} \times 100$$

***'Rhenus 1' known as 'Pyrodwarf' in Europe

TABLE 2

Fruit Size Grades Of Bartlett Pears Grown On Various Pear Rootstocks

| ROOT STOCK | NUMBER OF FRUIT IN VARIOUS SIZES* 45 | 50 | 55 | 60 | 65 | 70 | 75 | 80 | 85 |
|---|---|---|---|---|---|---|---|---|---|
| EM QUINCE A | 1 | 2 | 3 | 20 | 33 | 13 | 2 | 1 | 1 |
| EM QUINCE C | 2 | 5 | 19 | 21 | 3 | 2 | 0 | 0 | 0 |

TABLE 2-continued

Fruit Size Grades Of Bartlett Pears
Grown On Various Pear Rootstocks

| | | | | | | | | | |
|---|---|---|---|---|---|---|---|---|---|
| RHENUS 3 | 0 | 2 | 2 | 22 | 25 | 20 | 21 | 3 | 1 |
| RHENUS 1** | 0 | 0 | 0 | 0 | 34 | 49 | 10 | 10 | 2 |

| ROOT STOCK | WEIGHT (kg) | FRUIT NUMBER |
|---|---|---|
| EM QUINCE A | 14.2 | 76 |
| EM QUINCE C | 8.2 | 52 |
| RHENUS 3 | 19.2 | 96 |
| RHENUS1** | 19.8 | 105 |

*Size grades given in mm diameter. Year is 1989
**'Rhenus 1 known as 'Pyrodwarf' in Europe'

I claim:

1. A new and distinct variety of *Pyrus communis* plant named 'Rhenus 3' as herein shown and described.

* * * * *

UNITED STATES PATENT AND TRADEMARK OFFICE

CERTIFICATE OF CORRECTION

PATENT NO. : PP 12,771 P2
DATED : July 11, 2002
INVENTOR(S) : Helmet B. Jacob

It is certified that error appears in the above-identified patent and that said Letters Patent is hereby corrected as shown below:

Column 2,
Line 42, change "U.S." to -- (U.S. --

Column 3,
Line 27, change "147A" to -- 174A --
Line 37, change "with at apex" to -- width at apex --

Signed and Sealed this

Twenty-third Day of September, 2003

JAMES E. ROGAN
*Director of the United States Patent and Trademark Office*